United States Patent
Plotnikov et al.

(10) Patent No.: US 9,638,648 B2
(45) Date of Patent: May 2, 2017

(54) FLAW DETECTION USING TRANSIENT THERMOGRAPHY

(75) Inventors: Yuri Alexeyevich Plotnikov, Schenectady, NY (US); Harry Israel Ringermacher, Delanson, NY (US)

(73) Assignee: General Electric Company, Niskayuna, NY (US)

( * ) Notice: Subject to any disclaimer, the term of this patent is extended or adjusted under 35 U.S.C. 154(b) by 731 days.

(21) Appl. No.: 13/434,607

(22) Filed: Mar. 29, 2012

(65) Prior Publication Data
US 2013/0261989 A1    Oct. 3, 2013

(51) Int. Cl.
*G01N 25/72*    (2006.01)
*G01K 17/00*    (2006.01)

(52) U.S. Cl.
CPC .................... *G01N 25/72* (2013.01)

(58) Field of Classification Search
CPC .......... G01M 1/00; G01N 25/72; G01K 17/00
USPC ................................ 702/40; 374/5
See application file for complete search history.

(56) References Cited

U.S. PATENT DOCUMENTS

| | | | |
|---|---|---|---|
| 6,516,084 | B2 | 2/2003 | Shepard |
| 6,751,342 | B2 * | 6/2004 | Shepard ........................ 382/141 |
| 6,759,659 | B2 | 7/2004 | Thomas et al. |
| 7,057,176 | B2 | 6/2006 | Rothenfusser et al. |
| 7,389,206 | B2 | 6/2008 | Plotnikov |
| 7,485,882 | B2 | 2/2009 | Zombo et al. |
| 7,822,268 | B2 | 10/2010 | Rothenfusser et al. |
| 2007/0288177 | A1 * | 12/2007 | Rothenfusser et al. ........ 702/40 |
| 2008/0040053 | A1 * | 2/2008 | Plotnikov ........................ 702/38 |
| 2009/0245321 | A1 | 10/2009 | Ringermacher et al. |
| 2010/0033565 | A1 | 2/2010 | Benzerrouk et al. |
| 2011/0235672 | A1 | 9/2011 | Shepard et al. |
| 2011/0297829 | A1 * | 12/2011 | Altmann et al. .............. 250/332 |

* cited by examiner

*Primary Examiner* — Gregory J Toatley
*Assistant Examiner* — Ruihua Zhang
(74) *Attorney, Agent, or Firm* — Pabitra K. Chakrabarti

(57) ABSTRACT

A method and system for inspecting an object is provided. In accordance with embodiments of the method, a thermal excitation pulse is applied to an object undergoing evaluation. A transient thermal signal from the object is detected in response to the thermal excitation pulse. Two or more orthogonal functions are applied to the transient thermal signal based on a defined time interval to generate two or more orthogonal components. The object is assessed for defects at different depths using the two or more orthogonal components.

22 Claims, 7 Drawing Sheets

FLAW DETECTION USING TRANSIENT THERMOGRAPHY

BACKGROUND

The invention relates generally to inspection systems and, more particularly, to thermographic inspection systems for defect detection within an object.

It is typically desirable to detect cracks, inclusions, and/or delamination that may be internal within composite, metallic, and ceramic parts used for complex systems, such as may be used in vehicles, engines, or power generation equipment. Nondestructive evaluation (NDE) techniques may be utilized to inspect the internal structure of such components and systems. However, conventional NDE techniques may suffer from a variety of deficiencies. For example, to the extent that defects are to be identified beneath the surface of the part or component undergoing inspection, there may be an insufficient or unacceptable signal-to-noise ratio for the inspection signal in question with respect to defects that exist beyond a certain depth with respect to the surface.

Similarly, another issue that may arise in trying to identify defects beneath the surface of a component or part is the separation of defects by distance from the surface. Such separation and characterization may be particularly useful in contexts where the component or part undergoing testing includes discrete regions or laminations characterized by depth from the surface. However, in practice, it may be difficult to achieve a meaningful or useful separation of observed defects with sufficient resolution so as to characterize or sort the observed defects based on depth.

BRIEF DESCRIPTION

In one embodiment, a method is provided for evaluating an object. The method includes the act of applying a thermal excitation pulse to an object undergoing evaluation. A transient thermal signal from the object is detected in response to the thermal excitation pulse. Two or more orthogonal functions are applied to the transient thermal signal based on a defined time interval to generate two or more orthogonal components. The object is assessed for defects at different depths using the two or more orthogonal components.

In an additional embodiment, a processor-based system is provided. The processor-based system comprises a storage encoding one or more processor-executable routines. The routines, when executed cause acts to be performed comprising: applying a thermal excitation pulse to an object undergoing evaluation; detecting a transient thermal signal from the object in response to the thermal excitation pulse; applying two or more orthogonal functions to the transient thermal signal based on a defined time interval to generate two or more orthogonal components; and assessing the object for defects at different depths using the two or more orthogonal components. The processor based system also comprises a memory configured to encode the one or more processor-executable routines prior to execution; and a processing component configured to access and execute the one or more routines when encoded by the memory.

In a further embodiment, one or more non-transitory computer-readable media are provided. The computer-readable media encode one or processor-executable routines. The one or more routines, when executed by a processor, cause acts to be performed comprising: applying a thermal excitation pulse to an object undergoing evaluation; detecting a transient thermal signal from the object in response to the thermal excitation pulse; applying two or more orthogonal functions to the transient thermal signal based on a defined time interval to generate two or more orthogonal components; and assessing the object for defects at different depths using the two or more orthogonal components.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As discussed in detail below, embodiments of the present invention function to provide an inspection system that allows enhanced flaw detection of internal defects using transient thermography. Transient thermography involves observing the temperature distribution on the surface of an object as it is subjected to a pulse of heat (or heat sink) and then allowed to return to ambient temperature. In certain implementations, a component undergoing evaluation undergoes pulsed (i.e., flash) excitation resulting in a rapid increase of the temperature of the surface of the component.

The subsequent transient thermal response is gathered using an infrared sensing device or other temperature sensitive device.

In one implementation, this time-dependent response is digitized and transferred to a processing component for subsequent processing. A time interval is defined for processing. As discussed herein, the length of the time interval defines the fundamental frequency of a given integral transform. For each time processing interval, a complex plane signal representation is generated, such as by applying at least two orthogonal functions to the transient thermal response. The discrete integral transforms are used to map out amplitude and phase of the resulting complex values on the impedance plane for a selected frequency. In certain implementations, several higher frequency harmonics can be used in the post-processing analysis, such as to generate representations at different discrete depths within the object. Parameters that may be provided as inputs to the flaw detection analysis include, but are not limited to, time for processing (i.e., time interval), delay from the pulsed excitation to the processing interval, and the phase parameter used for the transform. The flaw detection methodology and systems discussed herein allow for fast multi-frequency and phase analysis after a single excitation pulse and provide enhanced flaw detection of a particular depth under a component surface. Examples of flaws that may be detected and/or distinguished from one another include, but are not limited to, inclusion, delamination, porosity, and so forth. Additionally, phase adjustment can be used to enhance image contrast or focus on a depth of interest.

In certain embodiments, the enhanced flaw detection of a particular depth under the surface of the component is achieved by generating multiple two-dimensional (2D) images from each processing time interval. In such an embodiment, phasegrams (phase versus pixel position in a 2D image) can be generated and used for analysis of the component. Phase rotation can be used to separate defects by depth of their location in the component.

Figure 1:
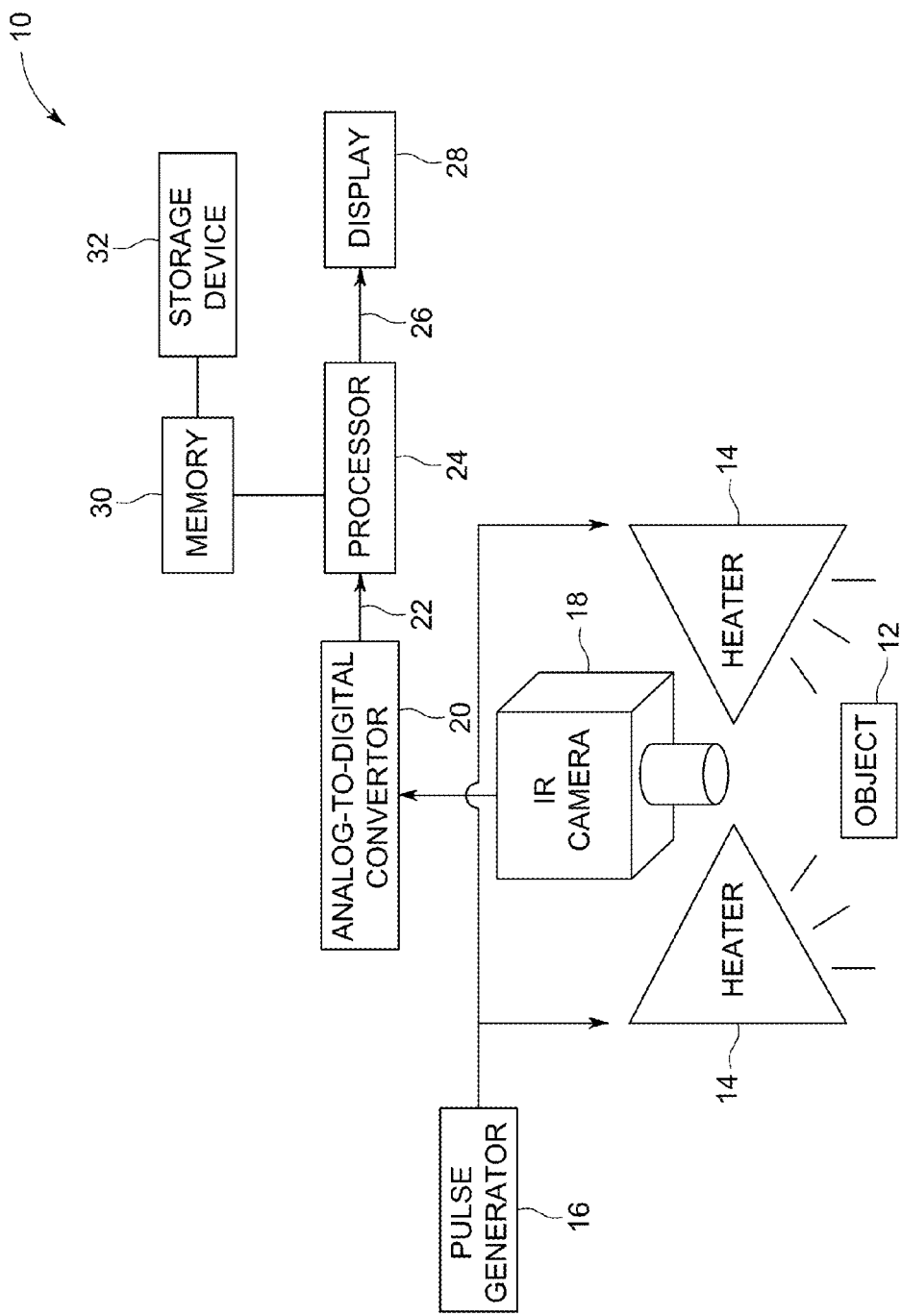
FIG. 1 is a diagrammatical representation of a thermography inspection system in accordance with an embodiment of the present disclosure.

With the foregoing in mind, FIG. 1 illustrates an infrared (IR) thermography inspection system 10 for inspecting an object 12 (such as a manufactured component or part) using heaters 14. The inspection system 10 includes a pulse generator 16 that is configured to supply a pulsed excitation to the heaters 14. The heaters 14 are configured to emit heat or radiative energy toward the object 12 so as to rapidly increase the temperature of the surface of the object 12. The infrared sensing device 18 senses temperature or IR energy emitted from the object 12 and generates an output signal corresponding to the transient thermal response of the object 12 over an interval of time. The pulsed excitation introduces a wide range of frequencies (f) into the object 12 under test. In addition, in the depicted embodiment the inspection system 10 includes an analog-to-digital converter 20 that is configured to digitize the output signal from the infrared sensing device 18 and to supply a digitized transient response signal such as represented by reference numeral 22 to a processor 24. As will be appreciated, in certain embodiments the analog-to-digital converter 20 may be provided as part of the infrared sensing device 18.

It should be noted that the present invention is not limited to any particular processor for performing the processing tasks of the invention. The term "processor," as that term is used herein, is intended to denote any machine capable of performing the calculations, or computations, necessary to perform the tasks of the invention. The term "processor" is intended to denote any machine that is capable of accepting a structured input and of processing the input in accordance with prescribed rules to produce an output. It should also be noted that the phrase "configured to" as used herein means that the processor is equipped with a combination of hardware and/or software for performing the tasks of the invention. In implementations where the processor 24 is a general purpose processor, such as may be found in a general purpose computer or workstation, the processor 24 may access and execute routines encoded by (or otherwise stored in) a memory 30 and/or storage device 32. The routines accessed and executed by the processor 24 in this manner may cause the performance of some or all of the various steps discussed herein for enabling flaw detection within the object 12. Conversely, in other embodiments the processor 24 may include or may be a special purpose processor or application specific integrated circuit (ASIC) device where certain of the functionality discussed herein is implemented via specific hardware structures or firmware.

The processor 24 is configured to convolve the digitized transient thermal response signal 22 with a number of orthogonal functions to generate a number of orthogonal components, as discussed herein. In one embodiment, the orthogonal functions include sine and cosine functions. In certain embodiments, the infrared sensing device 18 may be attached to a two-dimensional mechanical raster scanner to obtain transient responses from different, discrete positions over the object 12 as controlled by the scanner. In such an embodiment, the processor 24 is configured to generate a number of linear profiles that correspond to the sensing device positions controlled by the mechanical scanner using the orthogonal components. Moreover, a two-dimensional plot of the linear profiles may be made available to a user via a display 28 coupled to the processor 24. For example, the display 28 may be used to display an XY scatter plot of the linear profile in a complex plane that is generated from the orthogonal components generated by the system 10. As will be appreciated, the processor 24 may implement or execute computational algorithms with embedded digital or analog signal processing for convolving the digitized transient thermal response signals 22 and generating the linear profiles from the orthogonal components.

While FIG. 1 depicts a processor-based implementation, other embodiments may include a hardware-based implementation via integrated circuit electronics. For example, in alternative embodiments, an array of integrators may be employed that are configured to receive the output signal from the sensing device 18 and to convolve the output signal with a number of functions to generate a plurality of orthogonal components, as discussed above. In one such implementation, the integrators are configured to convolve the output signal at a number of frequencies to generate a plurality of orthogonal components that each correspond to a respective depth in the object 12. In such embodiments, the integrators or other implementation circuitry may be integrated into the front-end electronics with embedded digital or analog processing. Consequently, in such embodiments a high-speed digitizer or programmable processor may not be needed to perform the mathematical computations associated with more complex analytical functions, such as sine and cosine functions.

Figure 2:
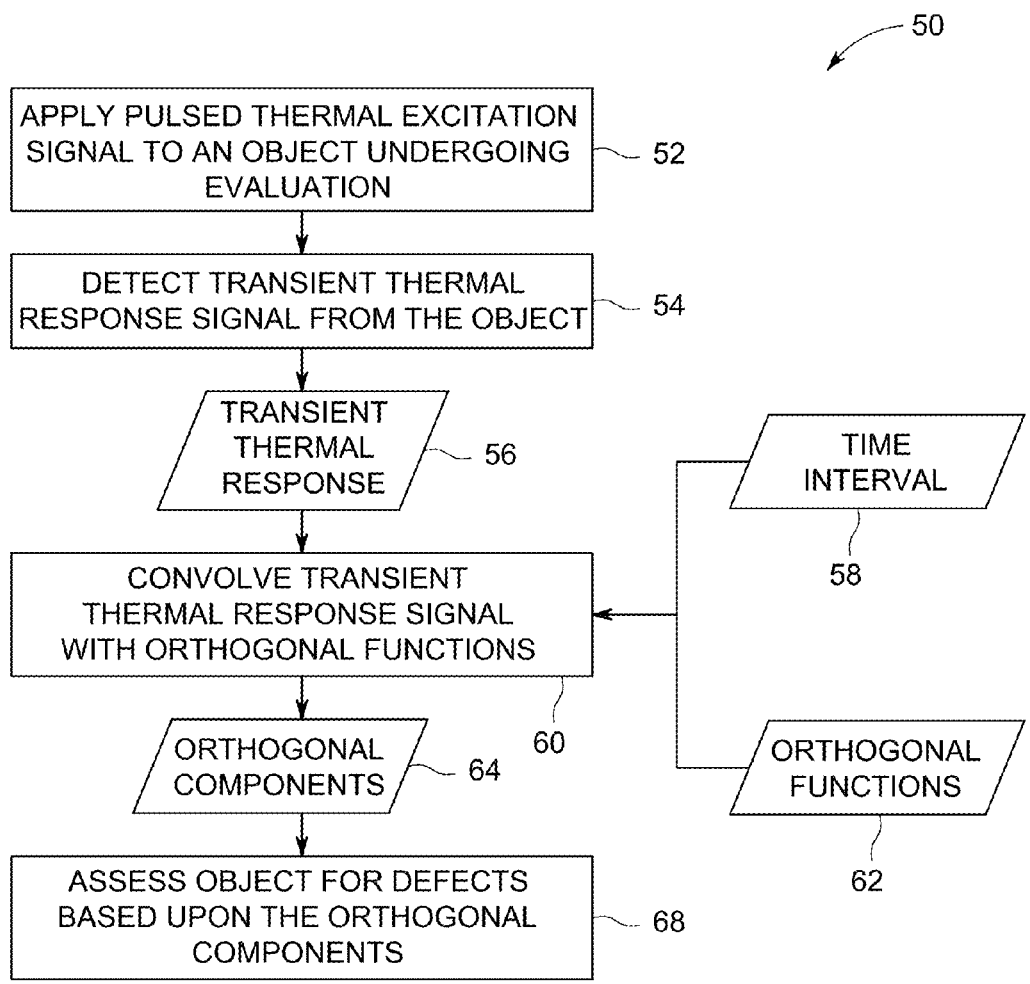
FIG. 2 is a flow chart illustrating a method for inspecting an object using the inspection system of FIG. 1, in accordance with an aspect of the present disclosure.

Turning to the next figure, FIG. 2 is a flow chart illustrating a method 50 for inspecting an object 12 (FIG. 1) using the inspection systems of FIG. 1. As illustrated, a pulsed thermal excitation is applied (block 52) to an object 12. A transient thermal response signal 56 generated in response to the pulsed excitation is detected (block 54). Based upon a specified time interval 58, the transient thermal response signal 56 is convolved (block 60) with orthogonal functions 62 to generate a respective orthogonal components 64 that may be associated with each time processing interval 58. As discussed herein, these orthogonal components 64 that may be used in assessing defects (block 68).

In one embodiment, the orthogonal functions 62 include a sine function and a cosine function. In one such embodiment, the sine function takes the form of a discrete sine transform and the cosine function is a discrete cosine transform. As will be appreciated, these examples are provided by way of illustration only and are not limiting. Any suitable function may be used in the processing of the transient thermal response 56 to generate the orthogonal components 64. More generally, the orthogonal (also called unitary, if complex) functions 62 may be any function $\phi_i$ defined in a≤x≤b that satisfies the general condition:

$$\int_b^a \phi_i(x)\phi^*_j(x)dx = K_i\delta_{ij} \quad (1)$$

where $\delta_{ij}=1$ for i=j, and =0 for i≠j, and * is the complex conjugate. The orthogonal components 64 generated from the transient thermal response signal 56 are representative of the presence or absence of one or more defects in the object, as discussed below.

In certain embodiments, a number of linear profiles are generated using the orthogonal components 64 that are graphed in a complex plane to generate a XY scatter plot (complex plane trajectories or Lissajous). In such an embodiment, defect detection (block 68) may be performed based upon the respective complex plane signal representations generated based upon the orthogonal components 64 for each respective processing time interval. In one embodiment, the complex plane is defined by the real axis oriented horizontally and the imaginary axis oriented vertically. In such an example, the discrete transforms are utilized to map real and imaginary components of the vector locus on the complex plane for a selected frequency. A phase shift (φ) is determined for the transient thermal response based upon a difference between an initial time ($T_O$) and a zero position of the sine function. Further, the linear profile or XY scatter plot may be adjusted using the phase shift (φ).

The generation of orthogonal components 64 from the transient thermal response signal 56 and defect detection based upon such orthogonal components 64 will be described below with reference to FIGS. 3-12.

Figure 3:
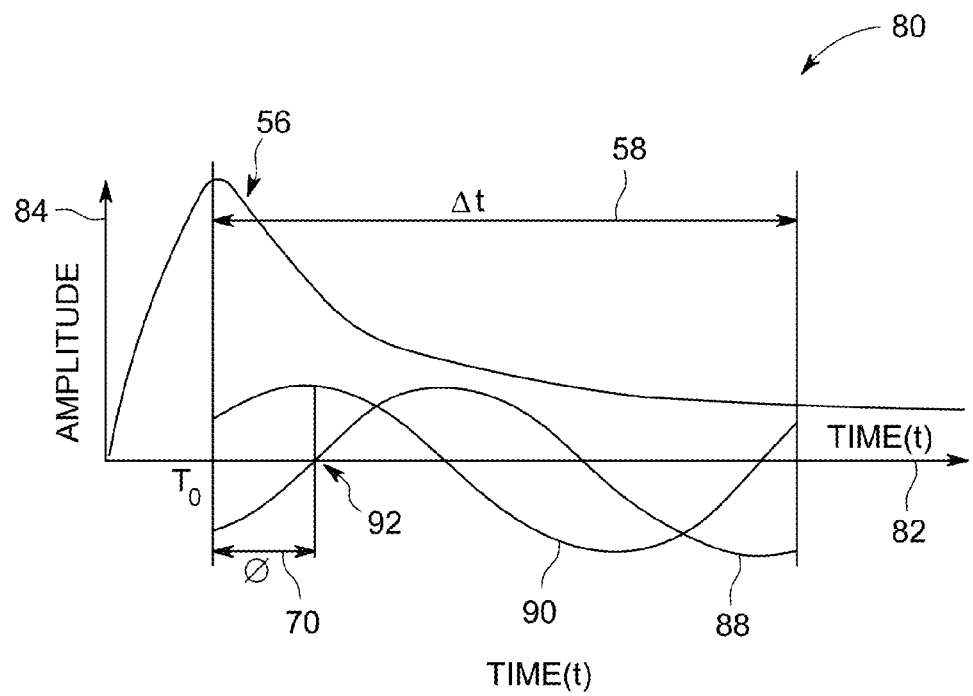
FIG. 3 is a graphical representation of a transient thermal response signal obtained using the inspection system of claim 1, in accordance with an aspect of the present disclosure.

Turning to FIG. 3, this figure is a graphical representation 80 of a transient thermal response signal obtained using the inspection system 10 of FIG. 1. In the illustrated embodiment, the abscissa axis 82 represents elapsed time (t) and the ordinate axis 84 represents amplitude of the thermal transient response as measured at one pixel (i, j). The transient thermal response signal received from the object 12 (FIG. 1) in response to the applied pulsed thermal excitation is indicated by reference numeral 56. As depicted in FIG. 3, the transient thermal response signal 56 decays over time, indicating the cooling (i.e., thermal decay) of the object undergoing evaluation over time. If the transient thermal response signal 56 is a linear function of temperature, then:

$$T(i,j,n)) = a_{i,j}T(x,y,t) + b_{i,j}. \quad (2)$$

In this exemplary embodiment, the transient response signal 56 is convolved with a sine function and a cosine function (i.e., orthogonal functions 62)) that are represented by reference numerals 88 and 90. In an implementation employing a general or special purpose processor, the transient thermal response signal 56 is digitized prior to convolving the transient response signal 56 with the orthogonal functions 88, 90. A variety of orthogonal functions 62 may be employed to convolve the transient thermal response signal 56 for generating the orthogonal components 64 for defect detection.

A processing time (Δt) 58 for the convolving step and a phase shift (φ) 70 are indicated in FIG. 3. It should be noted that the processing time (Δt) 58 may be selected for the convolving step and defines a fundamental frequency (f=1/Δt) of the orthogonal component. In certain embodiments, the processing time (Δt) 58 may be selected using conventional look-up tables for frequency for harmonic excitation techniques. In addition, the phase shift φ 70 for the transient thermal response signal 56 may be determined based upon an initial time ($T_O$) and a zero position 92 of the sine function 88. Such a phase shift φ may be further employed to adjust a two-dimensional plot or linear profiles generated using the orthogonal functions, as discussed herein.

Figure 4:
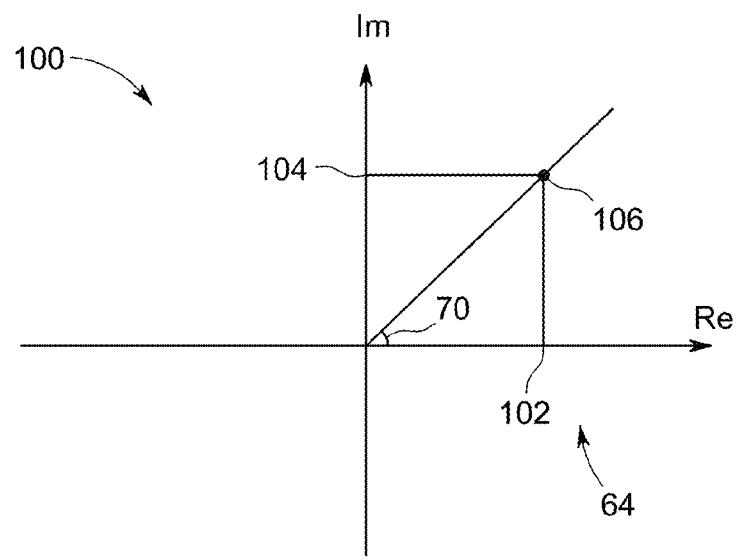
FIG. 4 is a graphical representation on a complex plane of a processed signal obtained by performing a discrete transform of the transient thermal response signal of FIG. 3, in accordance with an aspect of the present disclosure.

Turning to FIG. 4, this figure is a graphical representation 100 of orthogonal components 64 obtained by performing a discrete transform of the transient thermal response signal 56 of FIG. 3. As described above, the transient thermal response signal 56 is convolved with the discrete sine and cosine transforms to generate the orthogonal components 64. In certain embodiments, the orthogonal components 64 of the processed signal 106 include a real component ($S_{Re}$) 102 and an imaginary component ($S_{Im}$) 104. The real and imaginary components 102 and 104 for a given harmonic $k_w$ are represented by the following equations:

$$\text{Im}(i, j)|_{k_\omega} = -\frac{1}{N}\sum_{n=0}^{N-1} T(i, j, n)\sin\left(\frac{2\pi \cdot nk_\omega}{N}\right) \quad (3)$$

$$\text{Re}(i, j)|_{k_\omega} = \frac{1}{N}\sum_{n=0}^{N-1} T(i, j, n)\cos\left(\frac{2\pi \cdot nk_\omega}{N}\right). \quad (4)$$

As will be appreciated, the vector from origin (0) to point S 106 can be described as a periodic signal vector that rotates around the source point. The data, when transformed and represented in such a manner, no longer explicitly describes temperature response, though it does retain a relationship to temperature. In particular, the imaginary components 104, real components 102, phase φ 70, and magnitude of the vector define S.

As will be appreciated, phase differences observed in such plots correspond to different depths of defects (e.g., inclusions, pores, delaminations, and so forth). The phase value at a pixel having coordinates (i, j) is given by:

$$\phi(i, j) = \arctan\left(\frac{\text{Im}(i, j)}{\text{Re}(i, j)}\right). \quad (5)$$

As discussed below, this spatially localized depth information derived from the phase information may be used to generate plots and/or images in the image domain that may be used by a reviewer to identify and localize defects.

In one embodiment the discrete integral transforms are used to map out amplitude and phase of the resulting complex value on the impedance plane for a chosen frequency. Impedance plane trajectories (i.e., Lissajous plots) generated from such orthogonal components 64 are graphed on the complex plane to represent a XY scatter plot of the orthogonal components 64. Alternately, the processed signal 106 can be characterized on the complex plane by phase 70 (angular measure) and magnitude (radial measure). It should be noted that the processed signal of the orthogonal components 64 represents the signal obtained by convolving the transient thermal response signal 56 at a first frequency ($f_1=1/\Delta t_1$). In certain embodiments, the convolving step may be repeated for a number of frequencies represented by:

$$f_1 = \frac{1}{\Delta t_1}, f_2 = \frac{1}{\Delta t_2}, \dots, f_n = \frac{1}{\Delta t_n} \quad (6)$$

to generate sets of orthogonal components, where each of the sets of orthogonal components corresponds to a respective depth ($\Delta z$) in the object.

The generation of the sets of orthogonal components 64 for defect detection of a multi-layered object is described is greater detail below. In certain of the described examples, data was collected using the present approach on composite fiber reinforced plastic (CFRP) multi-layer plate with inclusions at different layers. Certain of these figures depict the formation of linear profiles and 2D images as a function of depth of inclusions. Potential input parameters include time for processing, delay from the pulse excitation to the processing interval and phase parameter used for the transform. The length of the processing (i.e., time interval), as discussed above, defines the fundamental frequency of a given integral transform. In certain implementations, several higher frequency harmonics can be used in the post-processing analysis.

For enhanced flaw detection at a particular depth under the surface, multiple 2D images are also described and are generated from each processing time interval or from combinations of time intervals. As shown in certain of the figures, phasegrams (phase versus pixel position in a 2D image) can be generated and used for analysis of a component corresponding to a representative thermogram of the acquired data. As discussed above, phase rotation can be used to separate defects by the depth of their location in the component.

Figure 5:
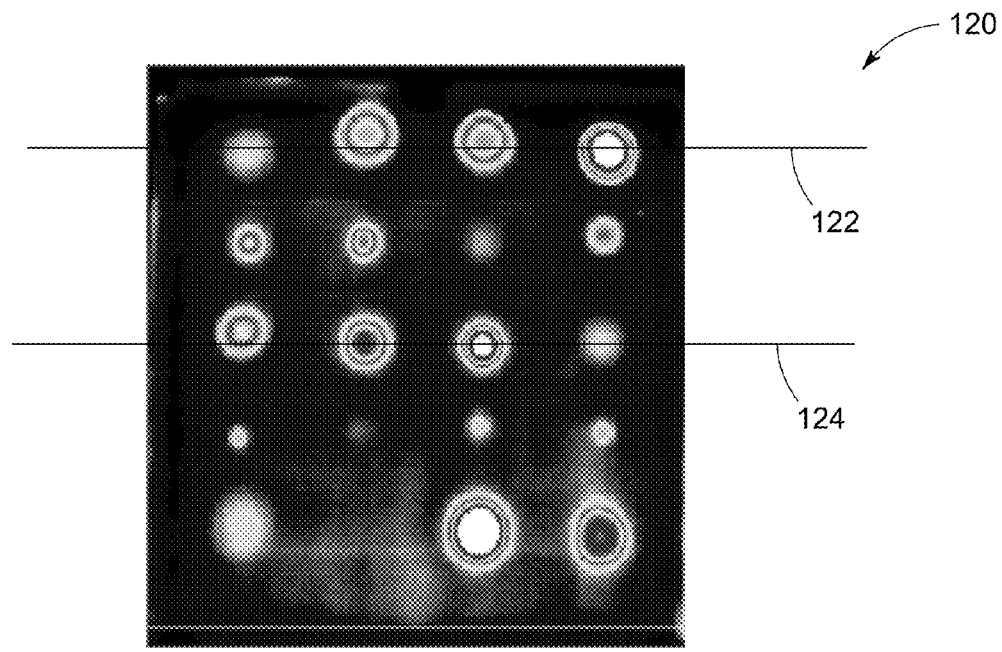
FIG. 5 is a thermal amplitude image depicting defects at different layers within an object, in accordance with an aspect of the present disclosure.

Turning to FIG. 5, a 2D thermal image 120 is depicted along with corresponding complex plane XY scatter plots (FIGS. 6 and 7), as discussed above, that are each derived for a corresponding line of pixels (lines 122, 124) in the 2D thermal image 120. In the present example, the 2D thermal image 120 is of a multi-layer test substrate (e.g., composite fiber reinforced plastic (CFRP)) having inclusions at different planar locations and at different depths (i.e., layers). The first respective XY scatter plot 130 is derived for a first row of pixels (corresponding to line 122) and is indicative of four different inclusions at different depths along the first row of pixels 122. Likewise, the second respective XY scatter plot 132 is derived for a second row of pixels (corresponding to line 124) and is indicative of four different inclusions at different depths along the second row of pixels 124.

Figure 6:
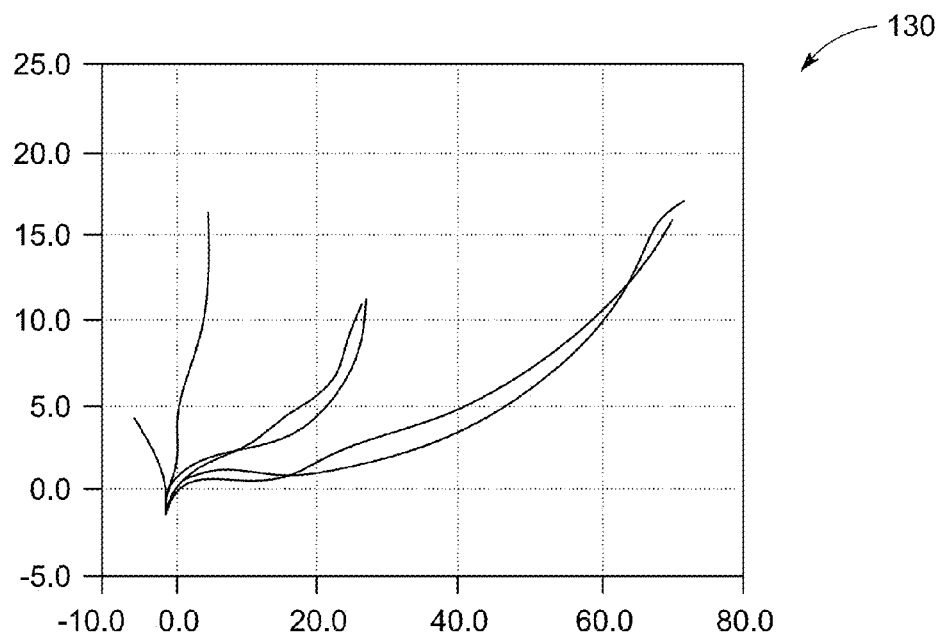
FIG. 6 is a first complex plane XY-scatter plot extracted for a first line of pixels in the image of FIG. 5, in accordance with an aspect of the present disclosure.
Figure 7:
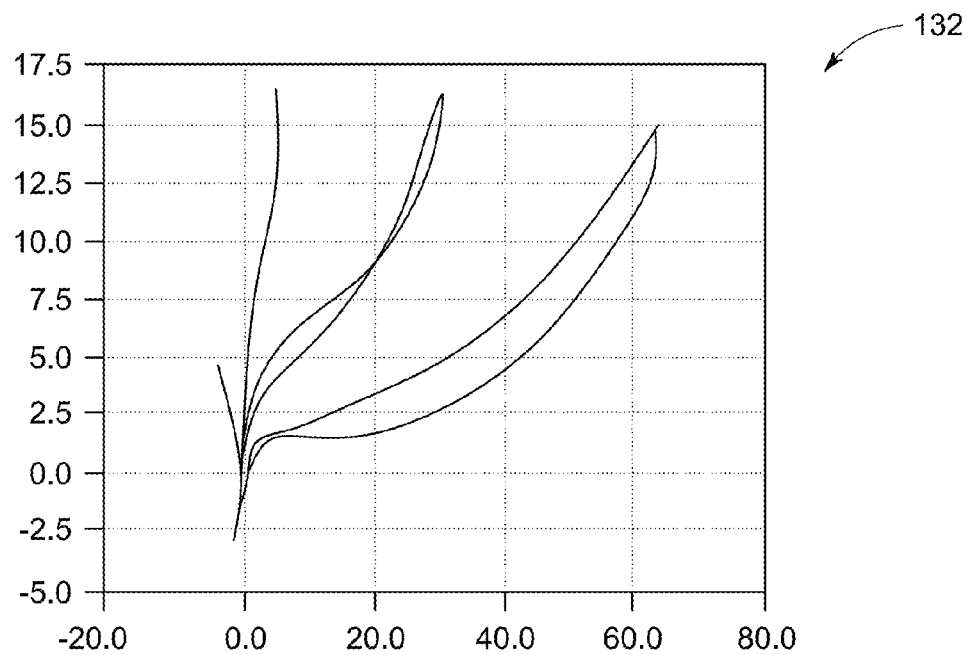
FIG. 7 is a second complex plane XY-scatter plot extracted for a second line of pixels in the image of FIG. 5, in accordance with an aspect of the present disclosure.
Figure 8:
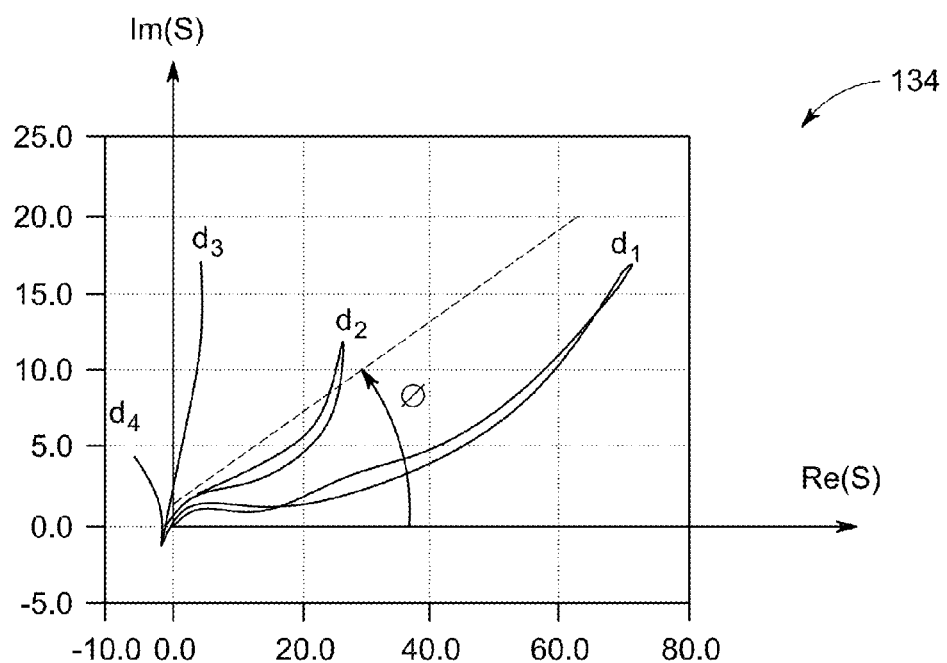
FIG. 8 is the first complex plane XY-scatter plot depicting differences in phase for defects of different depths, in accordance with an aspect of the present disclosure.

With this in mind, and turning to FIG. 8, the first XY scatter plot of FIG. 6 is depicted (plot 134) along with certain of the conventions of FIG. 4 to facilitate explanation and analysis. In this figure, depth discrimination of defects based on phase shift relative to the complex plane plot (as measured by $\phi$) is more clearly depicted. In particular, for the four defects ($d_1$, $d_2$, $d_3$, and $d_4$) depicted, the different respective phases for the corresponding vectors are indicative of different depths associated with the respective defects, with the extent of the phase shift corresponding to the depth of the defect. That is, the longer the phase shift difference, the deeper the defect.

Figure 9:
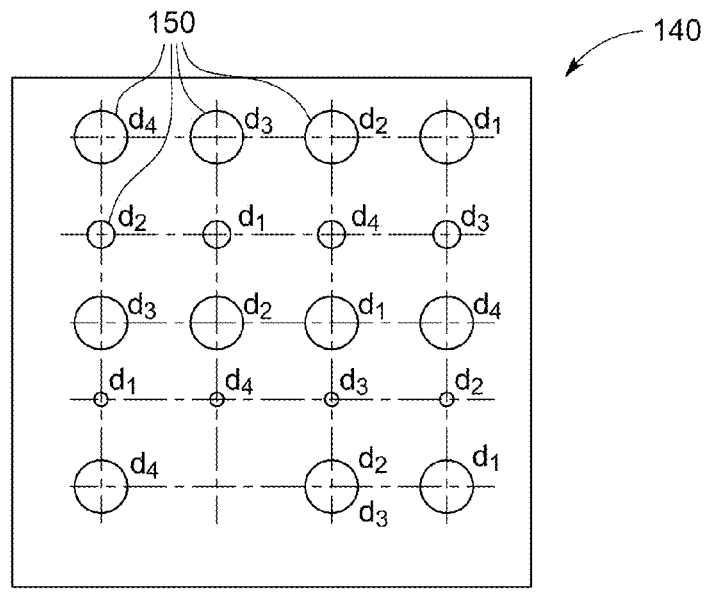
FIG. 9 is a schematic diagram depicting locations and relative size of defects at different layers within a test object, in accordance with an aspect of the present disclosure.
Figure 10:
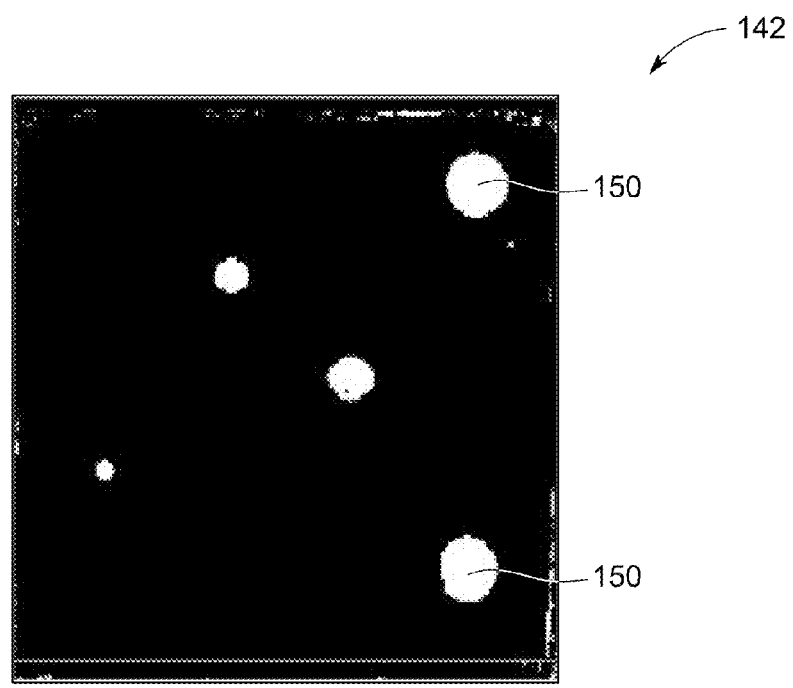
FIG. 10 is a multi-layer phasegram depicting defects observed at a first depth within the test object of FIG. 9, in accordance with an aspect of the present disclosure.
Figure 11:
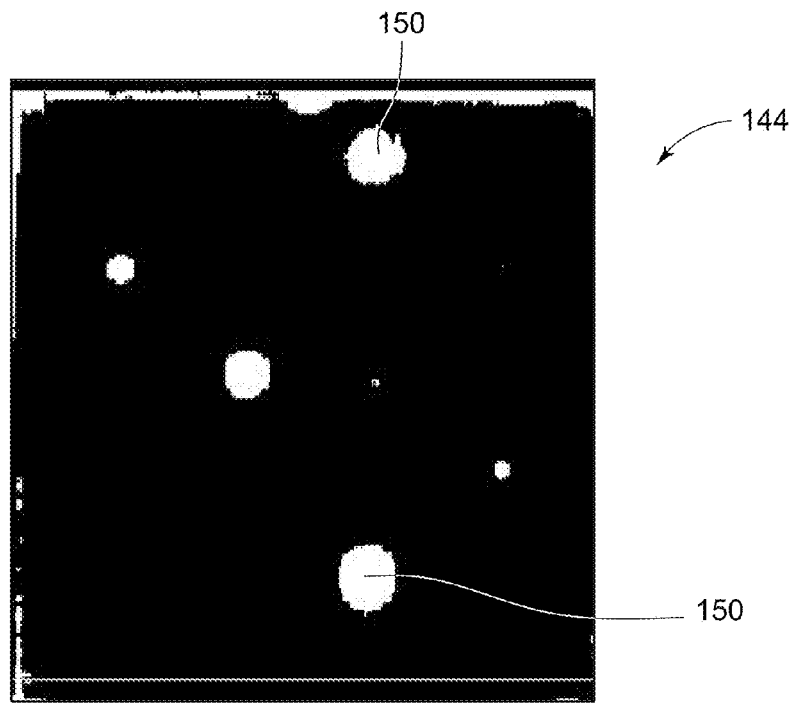
FIG. 11 is a multi-layer phasegram depicting defects observed at a second depth within the test object of FIG. 9, in accordance with an aspect of the present disclosure.
Figure 12:
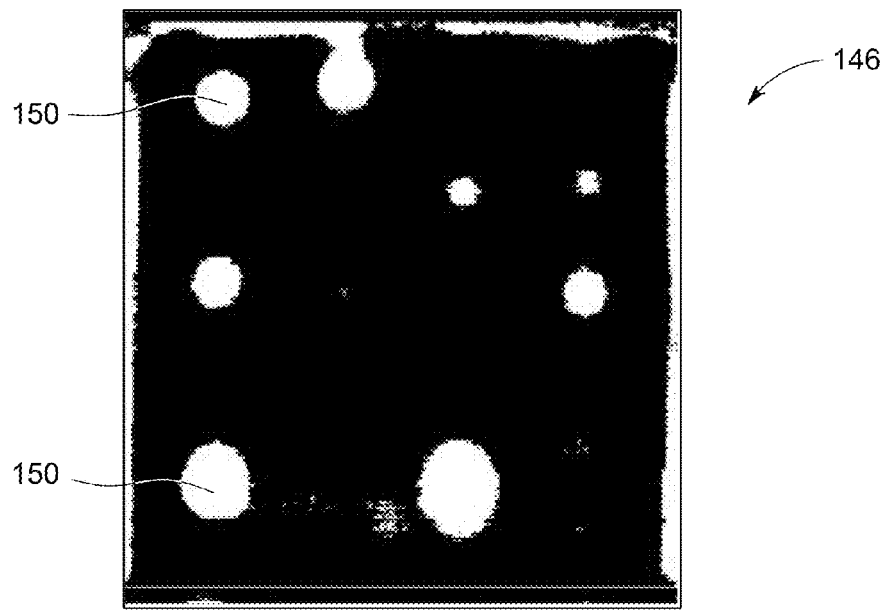
FIG. 12 is a multi-layer phasegram depicting defects observed at different discrete depths within the test object of FIG. 9, in accordance with an aspect of the present disclosure.

Turning to FIGS. 9-12, a test object and examples of multi-layer phasegrams are depicted in accordance with aspects of the present disclosure. In particular, in accordance with the depicted example, a multi-layer substrate having twenty defects 150 distributed on the various layers composing the substrate is schematically imaged (schematic diagram 140). This substrate and the respective defects 150 are illustrated in FIG. 9, which depicts the defect size, location and relative depth. Multi-layer phasegrams based on the transient thermal response derived for the substrate are also depicted in FIGS. 10-12. The multi-layer phasegrams are generated using multi-frequency processing and thresholding such that each phasegram corresponds to a different depth, layer, or lamination within the substrate undergoing evaluation.

That is, using phase shift and/or time delay (as will be appreciated, $\Delta\phi = \Omega \Delta T$), a depth specific data set (which may or may not explicitly correspond to a layer or lamination of the substrate) can be created using multiple frequencies of data and thresholding. For example, in terms of frequency, the higher the frequency, the shorter the distance and, therefore, the closer to the surface is the defect. As noted above, this frequency relationship to depth of defect can also be observed by looking at time instead of frequency, with a deeper layer corresponding to a longer or later time interval used in processing the transient thermal response signal 56.

Thus, each phasegram depicted in FIGS. 10-12 correspond to a different depth or lamination within the evaluated object. In these examples, each phasegram is depicted as a binary image, with a given pixel either having a value of 1 or 0 for a given layer or depth. Each phasegram may be defined or described by the number of processed frames and the time gate width (i.e., the processing time interval). For example, turning to FIG. 10, the respective phasegram 142 corresponds to a high frequency and is thresholded to only depict observed defects 150 in a first (i.e., highest) layer, $d_1$, or lamination computed for frames from number 14 to number 34. Thus, FIG. 10 visually depicts the spatial XY location of defects 150 present in the first or highest layer or lamination.

Conversely, based on the frequencies processed and the thresholding employed, the phasegram 144 of FIG. 11 depicts the spatial locations of defects 150 present in the second layer, $d_2$, or lamination computed for frames from 23 to 50, e.g., the layer or lamination immediately below that represented in FIG. 10. Further, turning to FIG. 12, a phasegram 146 is depicted showing defects 150 in two deeper layers, $d_3$ and $d_4$, or laminations computed for frames from 60 to 960, in this case the fourth and eighth layer or lamination. As will be appreciated, such a multi-layer phasegram may be constructed based on the frequencies processed and thresholding employed such that user can construct a phasegram reflecting defects in one layer or lamination or in some combination of layers or laminations.

Phasegrams generated in this manner can provide a useful tool for a reviewer to assess discrete levels within an object undergoing evaluation for defects. In particular, such phasegrams can provide the reviewer with a spatial reference for defects at different discrete depths within the object. The reviewer may then make informed decisions regarding the quality or suitability of the component or part being evaluated.

The technical and commercial advantages of the method disclosed here include improved capability of detecting and assessing internal defects within an object undergoing evaluation. Defect detection based on transient thermal response can be done after a single thermal pulse excitation. Additionally, phase adjustment can be used to enhance image contrast in thermal amplitude images (by constructing 2D images of horizontal or vertical components of the processed data) or to focus on a depth of interest. The above method can be suitably implemented in an IR or other thermal transient nondestructive system for composite, metallic, or ceramic parts or for pats of other suitable construction that provide a thermal transient response suitable for analysis.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for evaluating an object, comprising:
   applying a single thermal excitation pulse to an object undergoing evaluation;
   detecting a transient thermal signal from the object in response to the single thermal excitation pulse;
   based upon each specified processing time interval of a plurality of processing time intervals of the single thermal excitation pulse, convolving the transient thermal signal with two or more suitable orthogonal functions to generate two or more orthogonal components associated with the specified processing time interval; and
   assessing the object for defects at different depths under a surface of the object using the two or more orthogonal components based upon the plurality of processing time intervals, wherein the lengths of the selected processing time intervals each define a respective fundamental frequency of the orthogonal functions.

2. The method of claim 1, wherein the single thermal excitation pulse comprises a single pulse of heat and the transient thermal response is acquired over time as the object returns to ambient temperature.

3. The method of claim 1, wherein the two or more orthogonal functions comprise a sine function and a cosine function.

4. The method of claim 1, wherein assessing the object for defects comprises generating a plurality of complex plane trajectories by graphing in a complex plane the orthogonal components defined by a plurality of lines of pixels in a thermal amplitude image.

5. The method of claim 1, wherein detecting the transient thermal signal comprises processing an output of an infrared imager.

6. The method of claim 4, wherein the defects at different depths are distinguished based on different phases associated with the defects in one or more of the complex plane trajectories.

7. The method of claim 1, wherein the different depths of defects are further ascertained based on a frequency defined by the processing time interval or a time determined based upon a predetermined initial time and a predetermined position of at least one of the orthogonal functions.

8. The method of claim 1, wherein assessing the object for defects comprises generating two or more two-dimensional images, wherein each two-dimensional image depicts defects at different depths under the surface of the object within the object.

9. The method of claim 8, wherein each two-dimensional image depicts phase versus spatial pixel position.

10. A processor-based system, comprising:
    a storage encoding one or more processor-executable routines, wherein the routines, when executed cause acts to be performed comprising:
    applying a single thermal excitation pulse to an object undergoing evaluation;
    detecting a transient thermal signal from the object in response to the single thermal excitation pulse;
    based upon each specified processing time interval of a plurality of processing time intervals of the single thermal excitation pulse, convolving the transient thermal signal with two or more suitable orthogonal functions to generate two or more orthogonal components associated with the specified processing time interval; and
    assessing the object for defects at different depths under a surface of the object using the two or more orthogonal components based upon the plurality of specified processing time intervals, wherein the lengths of the selected processing time intervals each define a respective fundamental frequency of the orthogonal functions;
    a memory configured to encode the one or more processor-executable routines prior to execution; and
    a processing component configured to access and execute the one or more routines when encoded by the memory.

11. The processor-based system of claim 10, wherein assessing the object for defects comprises generating a plurality of complex plane trajectories by graphing in a complex plane the orthogonal components defined by a plurality of lines of pixels in a thermal amplitude image.

12. The processor-based system of claim 10, wherein detecting the transient thermal signal comprises processing an output of an infrared imager.

13. The processor-based system of claim 11, wherein the defects at different depths are distinguished based on different phases associated with the defects in one or more of the complex plane trajectories.

14. The processor-based system of claim 10, wherein assessing the object for defects comprises generating two or more two-dimensional images, wherein each two-dimensional image depicts defects at different depths under the surface of the object within the object.

15. One or more non-transitory computer-readable media encoding one or more processor-executable routines, wherein the one or more routines, when executed by a processor, cause acts to be performed comprising:
    applying a single thermal excitation pulse to an object undergoing evaluation;
    detecting a transient thermal signal from the object in response to the single thermal excitation pulse;
    based upon each specified processing time interval of a plurality of processing time intervals of the single thermal excitation pulse, convolving the transient thermal signal with two or more suitable orthogonal functions to generate two or more orthogonal components associated with the specified processing time interval; and
    assessing the object for defects at different depths under a surface of the object using the two or more orthogonal components based upon the plurality of specified processing time intervals, wherein the lengths of the selected processing time intervals each define a respective fundamental frequency of the orthogonal functions.

16. The one or more non-transitory computer-readable media of claim 15, wherein assessing the object for defects comprises generating a plurality of complex plane trajectories by graphing in a complex plane the orthogonal components defined by a plurality of lines of pixels in a thermal amplitude image.

17. The one or more non-transitory computer-readable media of claim 15, wherein detecting the transient thermal signal comprises processing an output of an infrared imager.

18. The one or more non-transitory computer-readable media of claim 16, wherein the defects at different depths are distinguished based on different phases associated with the defects in one or more of the complex plane trajectories.

19. The one or more non-transitory computer-readable media of claim 15, wherein assessing the object for defects comprises generating two or more two-dimensional images, wherein each two-dimensional image depicts defects at different depths under the surface of the object within the object.

20. The method of claim 1, wherein assessing the object for defects comprises assessing the object for defects based on a delay from the single thermal excitation to the processing time interval.

21. The processor-based system of claim 10, wherein assessing the object for defects comprises assessing the object for defects based on a delay from the single thermal excitation to the processing time interval.

22. The one or more non-transitory computer-readable media of claim 15, wherein assessing the object for defects comprises assessing the object for defects based on a delay from the single thermal excitation to the processing time interval.

* * * * *